(12) United States Patent
Munk

(10) Patent No.: US 6,281,975 B1
(45) Date of Patent: Aug. 28, 2001

(54) CAPILLARY FLOW CELL WITH BULBOUS ENDS

(75) Inventor: Miner N. Munk, Sonoma, CA (US)

(73) Assignee: Eldex Laboratories, Inc., Napa, CA (US)

(*) Notice: Subject to any disclaimer, the term of this patent is extended or adjusted under 35 U.S.C. 154(b) by 0 days.

(21) Appl. No.: 09/521,071

(22) Filed: Mar. 7, 2000

(51) Int. Cl.⁷ .................................................. G01N 21/00
(52) U.S. Cl. ............................................ 356/440; 356/246
(58) Field of Search .................................... 356/244, 246, 356/440, 344; 250/341, 576; 422/82.05, 82.09

(56) References Cited

U.S. PATENT DOCUMENTS

| | | |
|---|---|---|
| 3,236,602 | 2/1966 | Isreeli .................................. 23/253 |
| 4,747,687 | 5/1988 | Hoppe et al. ........................ 356/246 |
| 4,886,356 * | 12/1989 | Paradis ................................ 356/246 |
| 4,983,038 * | 1/1991 | Ohki et al. ........................... 356/246 |
| 5,057,216 | 10/1991 | Chervet ............................... 210/198.2 |
| 5,274,227 | 12/1993 | Moring ................................ 250/227.25 |
| 5,300,779 * | 4/1994 | Hillman et al. ...................... 250/341 |
| 5,434,664 * | 7/1995 | Sapp .................................... 356/244 |
| 5,475,486 * | 12/1995 | Paoli .................................... 356/246 |
| 5,608,517 | 3/1997 | Munk ................................... 356/246 |
| 6,127,690 * | 10/2000 | Kitaoka ................................ 356/246 |

* cited by examiner

Primary Examiner—Hoa Q. Pham
(74) Attorney, Agent, or Firm—Thomason, Moser and Patterson

(57) ABSTRACT

A bent capillary flow cell with protruding end bulbs coaxial with centerline of an elongated center cylindrical section of capillary tubing. The bulbs provide a high light throughput entrance window for the cell. Light is piped along the elongated center section by total internal reflection at the outside surface of the cell wall. An external light absorbing band is placed in optical contact with outer surface of the cell wall over a transition cone region between the bulb and center cylindrical section of the cell. Each of the external light absorbing bands extend a short prescribed distance over the cylindrical wall to absorb light rays that would otherwise be light piped within the cell wall and have little exposure to the liquid in the cell.

11 Claims, 6 Drawing Sheets

CAPILLARY FLOW CELL WITH BULBOUS ENDS

BACKGROUND OF THE DISCLOSURE

1. Field of the Invention

The invention relates to a capillary flow cell that is used for light absorption measurements and, more particularly, to a bent capillary flow cell having bulbous ends to facilitate entry of light into the flow cell.

2. Description of the Background Art

Light absorption detectors for high performance liquid chromatography (HPLC) and capillary electrophoresis (CE) generally comprise four components: a light source, a means for selecting a narrow increment of wavelengths, a flow cell through which the sample to be analyzed and the light are passed, and a light sensor that measures the amount of light transmitted through the flow cell. When a light absorbing fluid sample passes through the flow cell, the amount of transmitted light decreases in accordance with Beer's Law;

$$\text{Beer's Law} \qquad \frac{I}{I_0} = 10^{-abc} \qquad (1)$$

where I is the transmitted light power, $I_0$ is the light power incident on the flow cell, a is absorptivity of the sample, b is the pathlength of the flow cell, and c is the sample concentration. The units of a, b, and c are chosen so that the product a b c is dimensionless. This product is defined as absorbance (A) and is the customary output of light absorption detectors. The absorbance output (A) of the detector increases in direct proportion to pathlength for a given change in sample concentration. But increasing the cell pathlength, without at the same time decreasing the cross sectional area of the cell, increases the volume of the cell and dispersion of the sample as the sample flows through the cell. This peak spreading is detrimental to the separating efficiency of the chromatographic or electrophoritic system in which the detector is used. For this reason, cells with capillary dimensions are sometimes used in HPLC and CE.

Chervet in U.S. Pat. No. 5,057,216 and Moring in U.S. Pat. No. 5,274,227 describe bent capillary flow cells where light absorption is measured in an elongated straight section of capillary tubing between two bends in the tubing. The sample containing liquid enters and leaves the flow cell via the two bends. Light is introduced into and extracted from the cell through the outside walls of the bends in the tubing. These bent capillary flow cells can offer a long liquid pathlength for the light, small cell volume, and a cleanly swept flow path through the flow cell. Chervet in U.S. Pat. No. 5,057,216 describes a method of manufacture and mounting a bent capillary flow cell, while Moring in U.S. Pat. No. 5,274,227 describes in detail the high degree of collimation and narrow width of the illuminating light beam required for efficient coupling of light into the liquid containing bore of the flow cell through the outside of a bend in the capillary tube. Moring also describes the angle and lateral offsets of the incident light beam with respect to the centerline of the elongated straight section on the bent capillary flow cell and maximum bend radius in order for the incident light beam to completely illuminate the bore of the elongated straight section of the cell.

The light throughput of a small aperture in an optical system T is approximately defined as $$T = n^2 A\Omega \qquad (2)$$

where n is the refractive index in the space where the aperture is located, A is the area of the aperture, and Ω is the solid angle included in the cone of light defined by limiting rays that pass through the aperture. It is desirable that a flow cell has high light throughput so that the light sensor and its amplifier electronics give a signal with a high signal-to-noise ratio (SNR). The narrow range of acceptance angles and the narrow lateral width of the illuminating light beam in the detector flow cells described by Chervet and Moring necessarily limit the light throughput of their flow cells. Furthermore, it is difficult to control and minimize the component of light that is lightpiped within the wall of the flow cell. This component of light travels almost entirely in the cell wall and has little exposure to the sample in the cell. As such, this stray light contributes to the noise of the detector without much contribution to signal. Additionally, this stray light can also severely limit the linearity of the detector response for a change in sample concentration. To illustrate this last point, assume that half of the incident light travels along the cell by light piping within the wall where the light absorbance of the sample is zero, and half of the incident light travels through and parallel to the cell bore where the absorbance is $A_0$. The absorbance measured by the detector according to Beer's Law (1) is $$A = -\log\left[\left(\frac{I_0}{2} + \frac{I_0}{2}10^{-A_0}\right)/I_0\right] = -\log\left[\frac{1}{2}(1 + 10^{-A_0})\right] \qquad (3)$$

The slope of the detector response curve is the derivative of A with respect to $A_0$.

$$\frac{dA}{dA_0} = \frac{1}{1 + 10^{+A_0}} \qquad (4)$$

The slope of the response curve is ½ for $A_0$ equal to 0 and is 1/11 for $A_0$ equal to 1. Clearly the detector response is highly nonlinear with change in $A_0$ which is itself proportional to change in sample concentration.

Therefore, there is a need in the art for an improved capillary flow cell.

SUMMARY OF THE INVENTION

The disadvantages of the prior art are overcome by the invention of a bent capillary flow cell with protruding end bulbs coaxial with centerline of an elongated center cylindrical section of a capillary tube. The bulbous ends provide a high light throughput entrance window for the cell. Light is piped along the elongated center section by total internal reflection at the outside surface of the cell wall. In addition, an external light absorbing band is placed in optical contact with outer surface of the cell wall over a transition cone region between the bulb and center cylindrical section of the cell. This external light absorbing band extends a short prescribed distance over the cylindrical wall of the center section to absorb light rays that would otherwise be light piped within the cell wall and have little exposure to the liquid in the cell.

BRIEF DESCRIPTION OF THE DRAWINGS

The teachings of the present invention can be readily understood by considering the following detailed description in conjunction with the accompanying drawings, in which.

To facilitate understanding, identical reference numerals have been used, where possible, to designate identical elements that are common to the figures.

DETAILED DESCRIPTION

Figure 1:
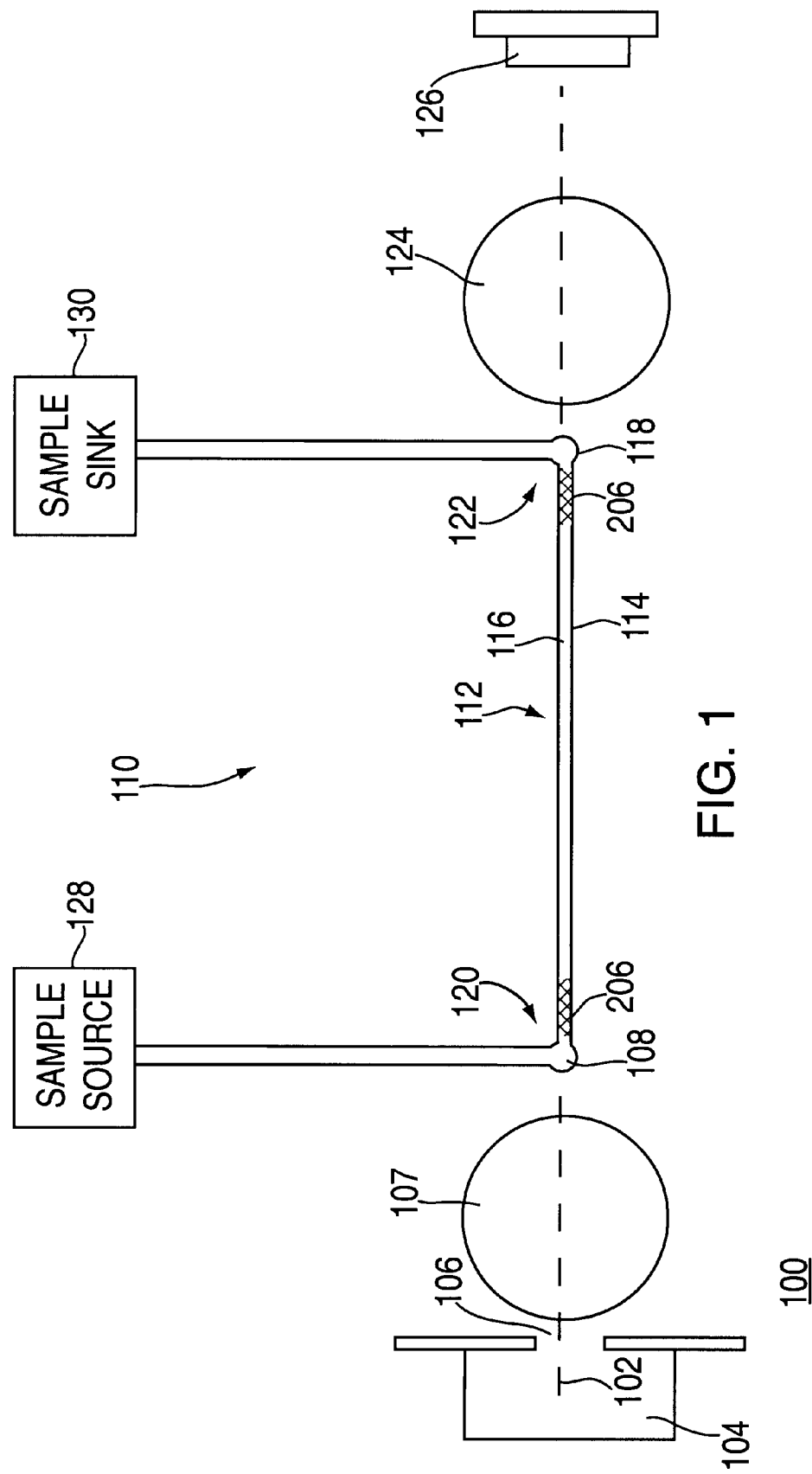
FIG. 1 depicts a light absorption detector including the flow cell of the present invention.

FIG. 1 depicts an embodiment of the present invention as used in a light absorption detector 100. The detector 100 comprises a light source 104, a first lens 107, a flow cell 110, a second lens 124, light absorbing bands 206, and a light detector 126. Coupled to the cell are a sample source 128 that supplies a liquefied sample to be measured and a sample sink 130 that sinks the sample after it flows through the cell. The first lens 107 focuses light 102 from an exit slit 106 of the light source (monochromator) 104 onto a bulb end 108 of the cell 110. The first lens 107 focuses the light to a point in the transition cone between the bulb end 108 of the cell and an elongated cylindrical center section 112 of the cell 110. The cell 110 has a bore 116 through the center section 112 that is filled with a liquid sample. Light passes through the liquid and is detected using second lens 124 and detector 126. In this manner, the absorbance of the sample is accurately measured.

More specifically, the light is piped along zig-zag paths in the liquid in the bore of the cell 110 and the cell wall 114 by total internal reflection at the outer surface of the cylindrical wall 114. The light exits the cell through the second bulb 118 and is focused on the active area of a light sensor 126 by second lens 124. Liquid, supplied by source 128, enters the cell 110 through one of the two bends 120 and exits the cell 110 through the other bend 122. As described below, in one embodiment of the invention, the light absorbing bands 206 are provided to limit "lightpiping" within the cell wall as the light propagates along the cell.

In another configuration (not shown), nearly parallel light from a wavelength selective filter is focused by first lens 107 through the bulb end 108 of the cell 110 to a point in the transition cone of the cell. In yet another configuration (not shown), second lens 124 is absent and a photosensor with sufficient active area to collect the unfocused light from the cell is positioned near the exit bulb 118.

First lens 107 and second lens 124 are shown as ball lenses. Hoppe and Munk in U.S. Pat. No. 4,747,685 describe some advantages for use of ball lenses with small volume flow cells for light absorption detectors. Most importantly, ball lenses are robust, inexpensive, and have relatively short focal lengths. Other types of lenses could be used as well, such as microscope objective lenses.

Additionally, the cell 110 could be in the U configuration where the two bends 120 and 122 are on the same side of the cell. Alternatively, the cell could be in a Z configuration where bends 120 and 122 are on opposite sides of the cell, or the cell could be in a more general configuration where bends 120 and 122 do not lie in the same plane.

Figure 2:
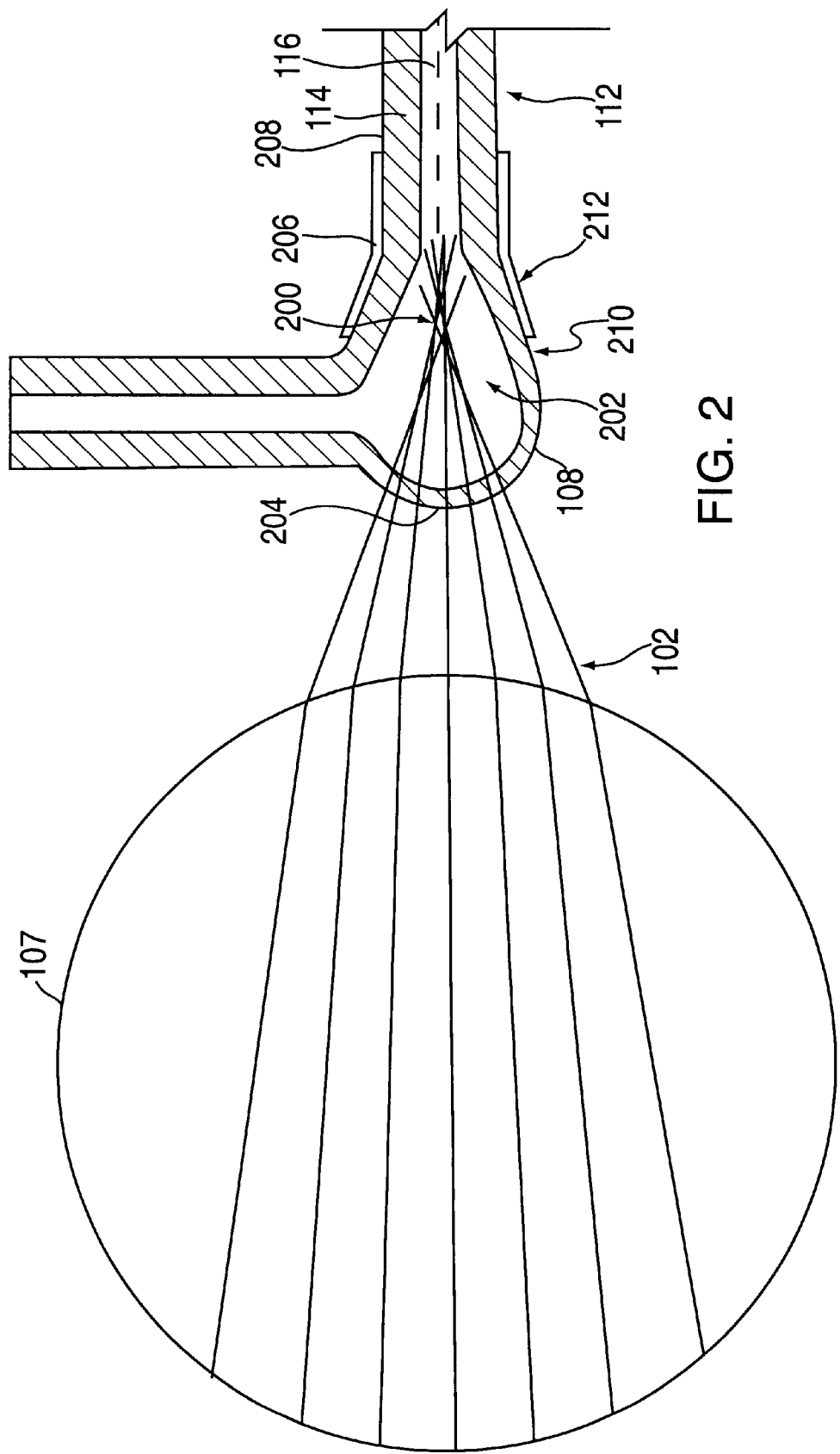
FIG. 2 depicts an enlarged longitudinal section of one end of the flow cell of FIG. 1.

FIG. 2 is an enlarged longitudinal section of the end 108 of the cell 110 where light 102 enters the cell 110. Light 102 enters the cell 110 through the protruding end of the bulb 108 and is focused by first lens 107 to a circle of least confusion 200 in the conical transition region 202 between the bulb 108 and the elongated cylindrical section 112 of the flow cell. The end surface 204 of the bulb 108 is the entrance window of the cell 110 for the light 102. The window is preferably spherical in shape, but could have other shapes such as spheroidal where the eccentricity of the generating ellipse is non-zero, or parabolic. Whatever the shape of the window, its center of revolution should be coaxial with the elongated cylindrical center section 112 of the flow cell 110. The external light absorbing band 206 is in optical contact with the outer surface 208 of the cell wall 114. This opaque external band is preferably light absorbing paint painted on the outer surface of the cell wall, but could be light absorbing polymer or eleastomer either fused to or pressed against the outer surface of the wall to make optical contact. This opaque external band 206 extends from near the large end 210 of the conical region 212, along the conical region 212, and for a short prescribed distance along the cylindrical section 112 of the cell 110. The approximately spheroidal entrance window 204 allows light rays with a wide range of converging angles to enter the cell and some to a focus at location 200. The inside diameters of the bulb 108 and transition cone regions 212 and 210 are larger than the cell bore 116 and present a larger effective entrance aperture for the cell 110 than would a bore of a capillary tube.

The large light acceptance angle and the enlarged effective entrance aperture of the bulb-end flow cell give this cell an inherently high light throughout. This high light throughput can only be maintained if the high angle rays propagate through the cell 110. If only those rays that propagate in a straight line through the cell bore propagated through the cells, the acceptance angle of these rays at the entrance to the cell of these rays would be very limited for long pathlength capillary flow cells. For example, if the cell had a bore diameter of 0.1 millimeter and a pathlength of 50 millimeters, the acceptance angle would be $\tan^{-1}(0.05/50)$ or about 0.06°. Higher angle rays, rays that make an angle larger than 0.06° with respect to the centerline of the cell, can only be propagated along the cell by reflecting from the wall of the cell. The most effective means of reflecting the rays is by total internal reflection at either the inner surface or the outer surface of the cell wall. Munk in U.S. Pat. No. 5,608,517 describes use of total internal reflection at the inner surface of the wall where the inside layer of the wall is made of a material having a low refractive index, such as a microporous amorphous fluorinated polymer. Because of its microporous nature, this polymer can cause contamination of the sample liquid in the cell due to either contaminants left in polymer after processing or previous samples that have contaminated the polymer. Additionally, cells with a microporous polymer inner surface tend to have long term drift problems. Isreeli in U.S. Pat. No. 3,236,502 describes use of total internal reflection at the outer wall surface of the cell where the cell wall is borosilicate glass and the atmosphere surrounding the cell is air. Total internal reflection at the outer wall surface does not require a potentially contaminating microporous polymer inner wall surface.

Figure 3:
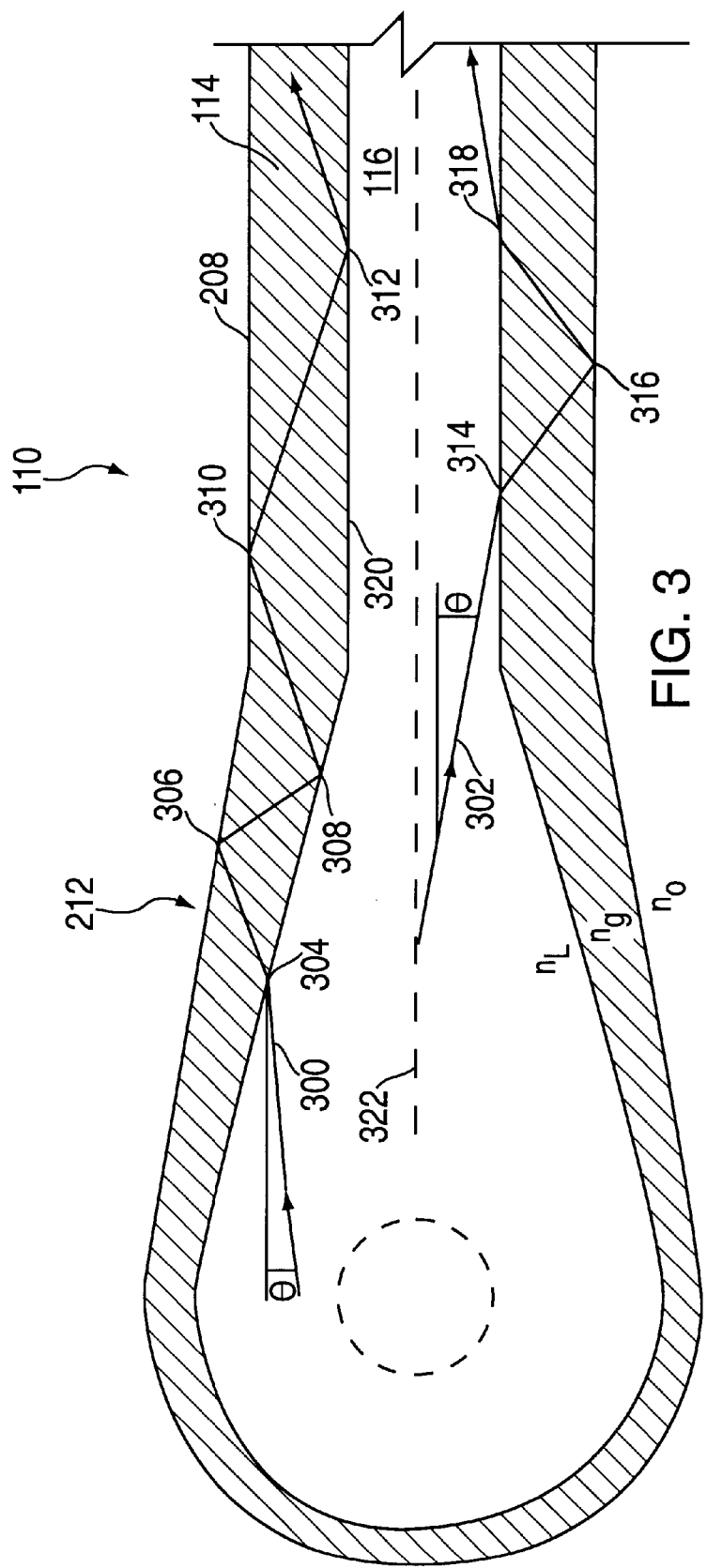
FIG. 3 depicts an enlarged longitudinal section of the entrance end of the flow cell of FIG. 1.

FIG. 3 is an enlarged longitudinal section of the entrance end of the flow cell 110 of this invention. For simplicity, the cell 110 is depicted without the external light absorbing band 206 (in FIG. 2). FIG. 3 depicts a cross section of the cell 110 taken in a meridional plane that contains the centerline of the flow cell that is orthogonal to the plane of FIG. 2. FIG. 3 shows the paths of two rays 300 and 302. Ray 300 intersects the inner surface 320 of the wall 114 at 304 in the conical transition region 212 of the cell 110 and is total internally reflected at points 306, 308, 310, 312 and at subsequent intersections with the inner and outer surfaces 208, 320 of the wall. In other words, ray 300 is light piped within the cylindrical wall 114 of the cell 110 and sees little exposure to the sample containing liquid in the cell 110. These rays that are light piped within the cell wall contribute undesirable stray light in the detector.

Figure 4:
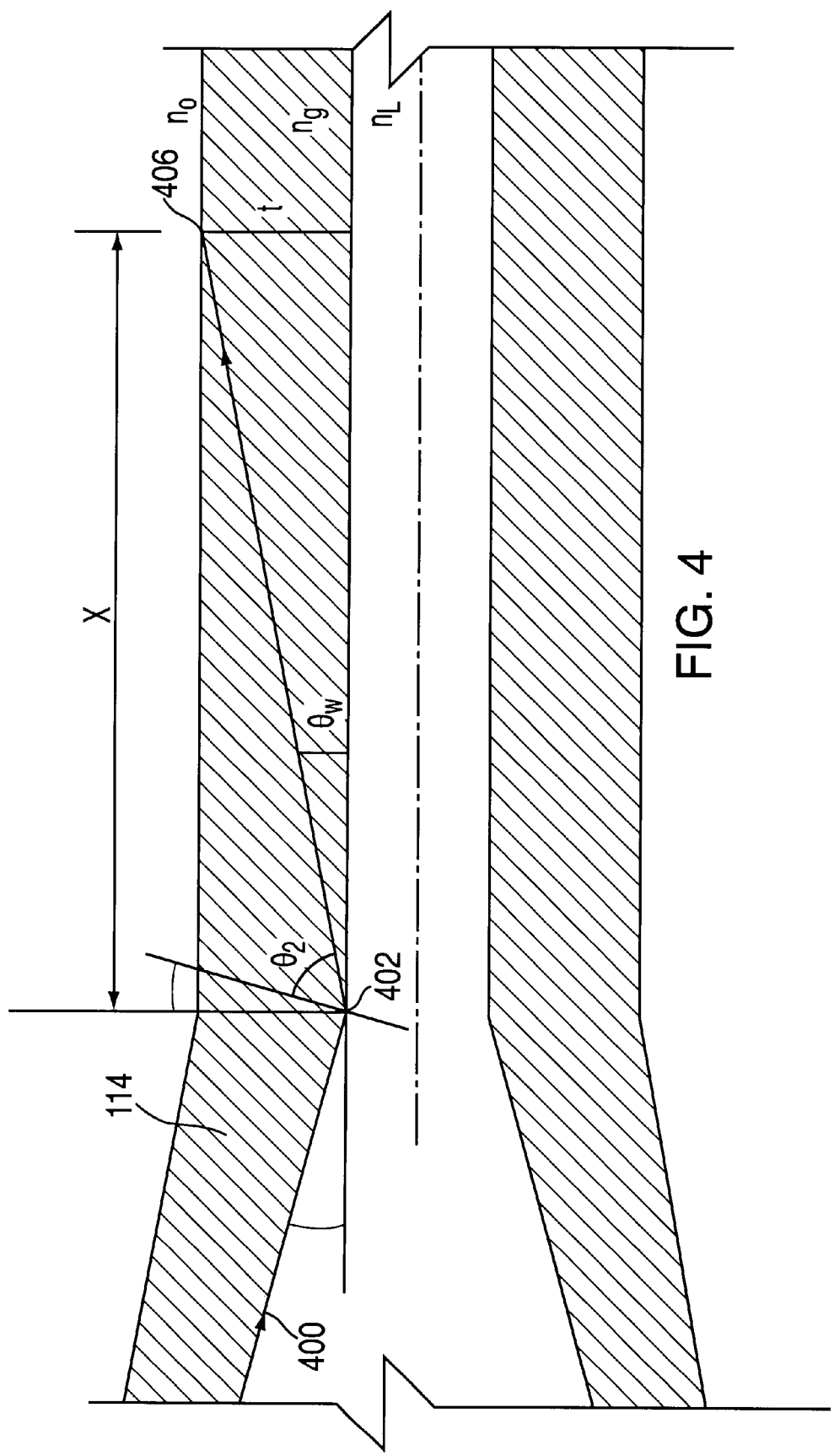
FIG. 4 depicts an enlarged longitudinal section of the conical transition portion the flow cell of FIG. 1.

One embodiment of the invention absorbs these light piped rays in the external light absorbing band (206 of FIG. 2) that covers the outside of the wall at 22 where the rays first intersect the outer surface 208 of the wall 114. This external light absorbing band should extend a distance x along the cylindrical cell wall to intercept the limiting ray 400 in FIG. 4. Ray 400 travels parallel to the inner cone surface and intersects the inner cone surface at its juncture with the cylindrical bore at 402. This ray 400 (a limiting ray) will be refracted into the wall at angle $\phi_2$ where $$\phi_2 = \sin^{-1}\frac{n_L}{n_g} \tag{5}$$

where $n_L$ is the refractive index of the liquid in the cell and $n_g$ is the refractive index of the wall 114. Limiting ray 400 will make an angle $\theta_W$ with respect to inner surface of the cylindrical wall where $$\phi = 90° - \phi_2 - \alpha - \phi_2 \tag{6}$$

a is the half-angle of the inner cone surface. The distance x from the junction of one of the conical and cylindrical regions that the external light absorbing band must extend to absorb ray 400 is $$x = \frac{t}{\tan\theta_w} \tag{7}$$

As an example, using 15° for the cone half-angle α, 1.36 for the refractive index of the liquid which is the refractive index of water at a wavelength of 250 nm, and 1.51 for the refractive index of the wall which is the refractive index of fused silica at a wavelength of 250 nm. In this example the distance x is $$x = 5.26t \tag{8}$$

where t is wall thickness. Based on the assumed values and a wall thickness of 0.1 mm, the light absorbing band would extend 0.526 mm from the junction of the inner cone surface and the cylindrical bore of the cell.

Returning to FIG. 3, ray 302 makes an angle θ with respect to the centerline 332 of the cell 110 and intersects the liquid-wall interface at 314 where the ray is refracted into the wall 114. If θ is less than $\cos^{-1}(n_0/n_L)$, the ray 302 is totally internally reflected at the outer surface 208 of the wall 114 at 316. Assuming that $n_L$ is 1.36 (approximately the refractive index of water at a wavelength of 250 nm) and $n_0$ is 1 (refractive index of air), the limiting angle of θ is 42.7°. Rays with angle θ less than 42.7° will be totally internally reflected at the outer cylindrical surface 208 of the cell 110. After reflection by the outer surface 208 of the wall 110, the ray 302 travels back through the wall 114 and be refracted into the liquid at an angle θ with respect to the centerline 322 of the cell 110. After refraction into the liquid, the ray 302 passes through the liquid to the opposite side of the wall and follow a mirror image of its previous pass through wall 114. This ray follows a zig-zag path along the cell 110. The light will be piped along the cell by successive total internal reflection at the outer surface 208 of the cell wall 114. Rays with different values of θ travel different distance in the liquid as they travel along the cell 110. Beer's Law (equation 1) assumes that all rays have equal pathlengths in cell 110, and unequal pathlengths cause the absorbance response of the detector to be nonlinear with sample concentration.

Typically there will be many half cycles between successive reflections at the outer wall 208 surface as a ray 302 travels in a zig-zag path along the cell 110. Therefore, the end effects caused by partial half cycles at the end of the cell can be ignored, and the relative liquid pathlengths for different values of θ are closely approximated by their relative liquid pathlengths in one half-cycle of the zig-zag path of the ray 302.

Figure 5:
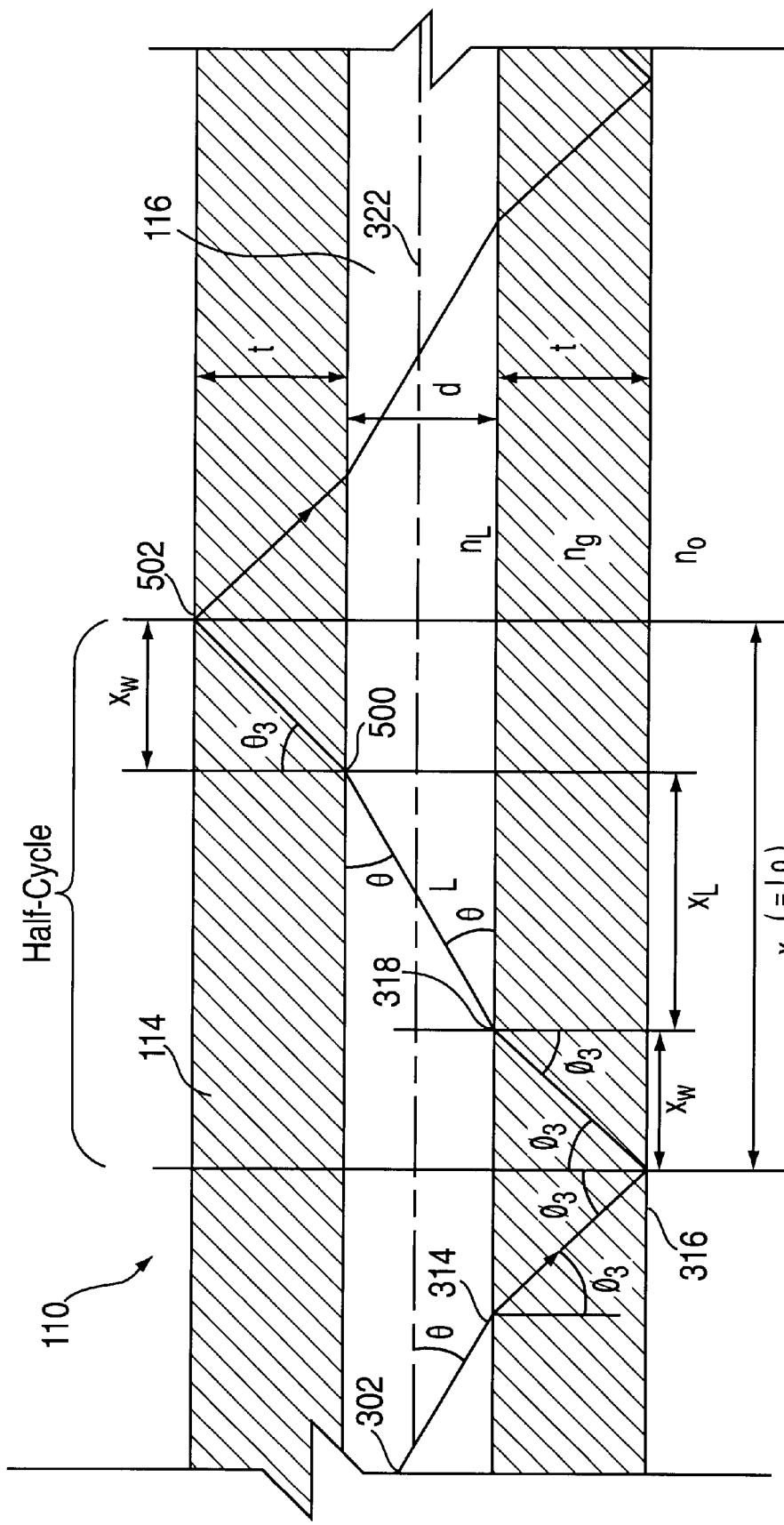
FIG. 5 depicts an enlarged longitudinal section of the cylindrical center section of the flow cell of FIG. 1.

The distance between successive intersections of ray 302 is the axial length of $x_0$ of one half-cycle of the rays zig-zag path along the cylindrical region 112 of the cell 110 as shown in FIG. 5. $\phi_3$ is the angle of refraction of the ray as it enters the wall from the central liquid in the cell 110, and φ is the angle the ray makes with the centerline 322 of the cell 110.

$$\phi_3 = \sin^{-1}\left(\frac{n_L}{n_g}\cos\phi\right) \tag{9}$$

The axial distance of the ray in one side wall 114 is $X_W$ and $x_W = t\tan\phi_3$ where t is the wall thickness The axial distance of the ray in bore of the cell is $x_L$ and $x_L = d/\tan\theta$ where d is the diameter of the cell bore The total axial distance for the ray in one half-cycle is $$x_0 = 2x_w + x_L \tag{10}$$

$$= 2t\tan\phi_3 + \frac{d}{\tan\theta}$$

and $x_0$ is the pathlength in liquid for a ray that travels along the centerline of the width θ=0.

The ratio of the pathlength in liquid for a ray with 0 to the pathlength of a ray that travels along the centerline of the bore width θ=0 is $$r = \frac{\frac{d}{\sin\theta}}{2t\tan\phi_3 + \frac{d}{\tan\theta}} \tag{11}$$

This ratio r depends on he refractive index of the liquid in the cell bore $n_L$ refractive index of the wall $n_g$, and the ratio of wall thickness t divided by the bore diameter d. The ratio r is computed from equations (7) and (11) by setting $n_L = 1.36, n_g = 1.51$, and t/d=0.5, 1.0, and 1.5. The results are presented in Table I.

TABLE I

| θ | r = L/x₀ | | |
|---|---|---|---|
| | t/d = 0.5 | t/d = 1.0 | t/d = 1.5 |
| 0° | 1.000 | 1.000 | 1.000 |
| 1° | 0.965 | 0.933 | 0.902 |
| 3° | 0.904 | 0.823 | 0.756 |
| 5° | 0.852 | 0.740 | 0.654 |

TABLE I-continued

| | r = L/x₀ | | |
|---|---|---|---|
| θ | t/d = 0.5 | t/d = 1.0 | t/d = 1.5 |
| 7° | 0.809 | 0.676 | 0.580 |
| 9° | 0.773 | 0.626 | 0.525 |

In order to estimate the absorbance response of a detector with these different pathlengths, the incident light $I_0$ is divided into five equal components with θ increments of 0° to 2°, 2° to 4°, 4° to 6°, 6° to 8°, and 8° to 10° and use the values in Table I for the relative pathlength in liquid for each of the θ increments. For example, the values for r for θ=3° for the angular θ increment from 4° to 6° are used to calculate the amount of light transmitted in this increment θ. This method of partitioning the incident light indicates the degree of nonlinearity of response of the detector due to the different pathlengths in liquid associated with light piping by the outer surface of the cylindrical wall. The light transmitted through each of the five increments $I_n$ is given by $$I_n = \frac{I_0}{5} 10^{-rA_0} \tag{12}$$

where $A_0$ is the absorbance for light that travels within and parallel to the cell bore. The measure absorbance of the detector is $$A_{meas.} = -\log I/I_0 = -\log \sum_{n=1}^{5} \frac{1}{5} 10^{-rA_0} \tag{13}$$

The calculated values of $A_{meas.}$ are presented in Table II for different values of $A_0$ with wall thickness to bore diameter ratios, t/b, of 0.5, 1.0, and 1.5.

TABLE II

| | $A_o = 0.001$ | $A_o = 0.01$ | $A_o = 0.1$ | $A_o = 0.2$ | $A_o = 0.5$ | $A_o = 1$ | $A_o = 2$ |
|---|---|---|---|---|---|---|---|
| t = 0.5 d | | | | | | | |
| $A_{meas.}$ | 0.0008608 | 0.008605 | 0.08601 | 0.17191 | 0.42898 | 0.85534 | 1.70061 |
| $A_{lin.}$ | 0.0008608 | 0.008608 | 0.08608 | 0.17215 | 0.43038 | 0.86076 | 1.72151 |
| % dev. | 0.00% | −0.03% | −0.08% | −0.24% | −0.33% | −0.63% | −1.21% |
| t = d | | | | | | | |
| $A_{meas.}$ | 0.0007607 | 0.007601 | 0.07587 | 0.15137 | 0.37643 | 0.74756 | 1.47256 |
| $A_{lin.}$ | 0.0007607 | 0.007607 | 0.07607 | 0.15214 | 0.38035 | 0.7607 | 1.5214 |
| % dev. | 0.00% | −0.08% | −0.26% | −0.51% | −1.03% | −1.73% | −3.21% |
| t = 1.5 d | | | | | | | |
| $A_{meas.}$ | 0.0006837 | 0.006831 | 0.06813 | 0.13586 | 0.33667 | 0.66391 | 1.29418 |
| $A_{lin.}$ | 0.0006837 | 0.006837 | 0.06837 | 0.13674 | 0.34184 | 0.86368 | 1.36737 |
| % dev. | 0.00% | −0.08% | −0.34% | −0.64% | −1.51% | −2.89% | −5.35% |

The values of $A_{lin.}$ listed in Table II are obtained by dividing the value $A_{meas.}$ (which is the calculated value of absorbance that the detector would measure) for $A_0$=0.001 by 0.001 and multiplying by the corresponding value of $A_0$.

$$A_{lin.} = \frac{A_{meas.} \text{ for } A_o = 0.001}{0.001} \times A_o \tag{14}$$

The percent deviation from a linear response is $$\% \, Dev. = \left(\frac{A_{meas.}}{A_{lin.}} - 1\right) \times 100 \tag{15}$$

Figure 6:
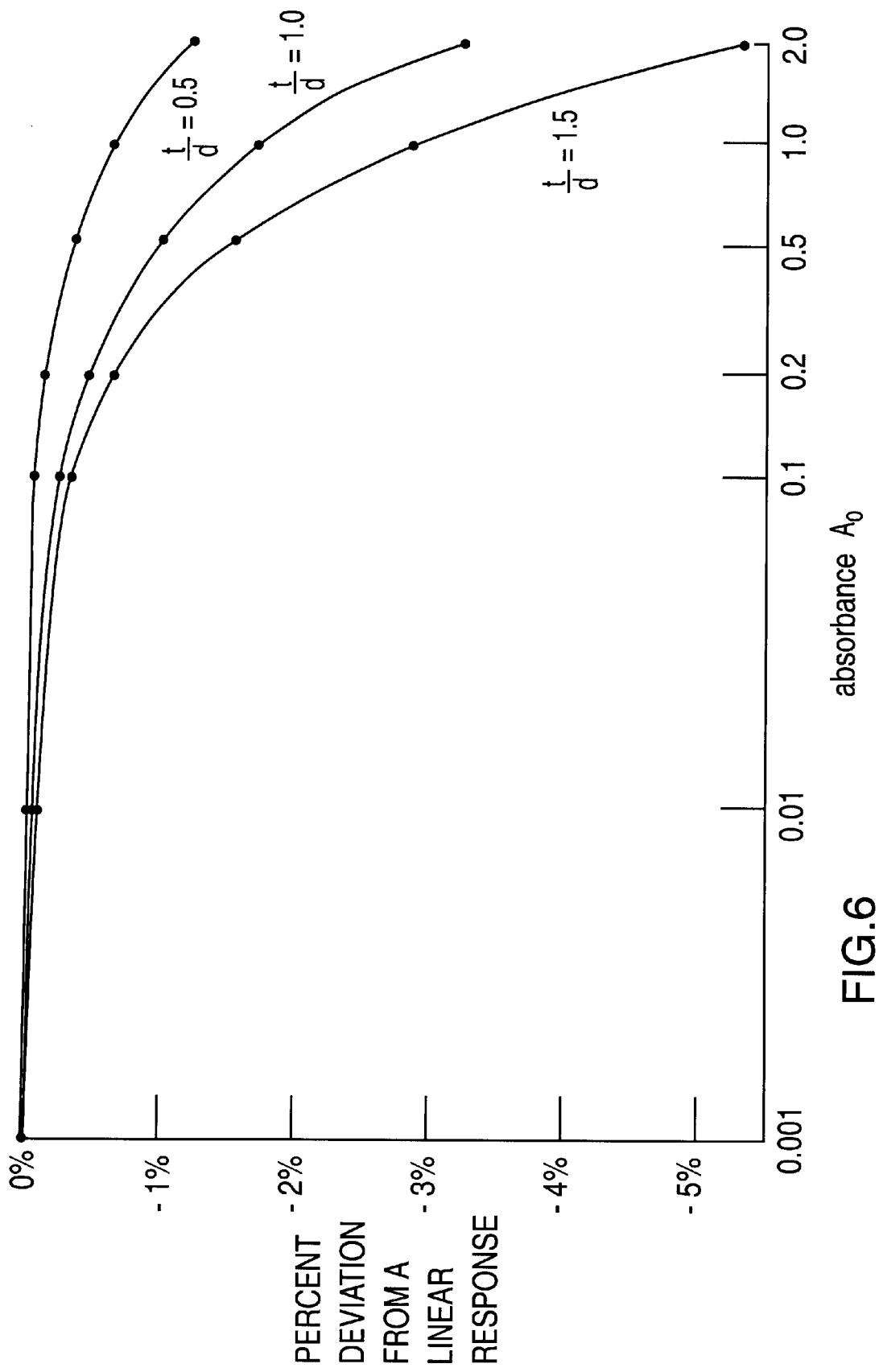
FIG. 6 depicts a graph of percent deviation from a linear absorbance response versus absorbance for three cell wall thickness to bore diameter ratios.

The calculated percent deviations from a linear response are listed in Table II and plotted against $A_0$ in a semilog plot in FIG. 6.

The upper limit of linear response of a light absorption detector is often defined as the absorbance at which the detector response deviates by either 1 percent or 5 percent from a linear response line through the lowest absorbance points where the detector is expected to give a linear response. The percent deviations listed in Table II and plotted in FIG. 6 suggest that, even for the largest wall thickness to bore diameter ratio considered of 1.5, the detector response is linear within 5 percent for absorbances up to 1 absorbance. A 5 percent deviation at 1 absorbance is generally acceptable for long pathlengths capillary flow cells.

Although various embodiments which incorporate the teachings of the present invention have been shown and described in detail herein, those skilled in the art can readily devise many other varied embodiments that still incorporate these teachings.

I claim:

1. A capillary flow cell comprising:
   a tube having a first bend and a second bend;
   a first bulb located at said first bend in said tube for receiving light; and
   a second bulb located at said second bend in said tube for allowing said light to exit said tube.

2. The capillary flow cell of claim 1 wherein said first and second bulbs comprise:
   a rounded surface for admitting light into said bulb;
   a conical section coupled between said rounded surface and a cylindrical tube section.

3. The capillary flow cell of claim 2 wherein at least a portion of said conical section and a portion of said cylindrical tube are covered with a light absorbing material.

4. The capillary flow cell of claim 2 wherein said rounded surface is spheroidal.

5. The capillary flow cell of claim 2 wherein said rounded surface is parabolic.

6. A sample absorbance measuring system comprising:
   a light source for supplying light;
   a first lens for focusing said light;

a capillary flow cell for receiving said focused light, comprising
a tube having a first bend and a second bend;
a first bulb located at said first bend in said tube for receiving said focused light; and
a second bulb located at said second bend in said tube for allowing said focused light to exit said tube; and
a light detector for detecting the light that exits the tube.

7. The system of claim 6 further comprising:
a second lens for focusing said light that exits said tube onto said detector.

8. The system of claim 6 wherein said first and second bulbs comprise:
a rounded surface for admitting light into said bulb;
a conical section coupled between said rounded surface and a cylindrical tube section.

9. The system of claim 8 wherein at least a portion of said conical section and a portion of said cylindrical tube are covered with a light absorbing material.

10. The system of claim 8 wherein said rounded surface is spheroidal.

11. The system of claim 8 wherein said rounded surface is parabolic.

* * * * *